(12) United States Patent
Roessl et al.

(10) Patent No.: US 9,625,589 B2
(45) Date of Patent: Apr. 18, 2017

(54) PHOTON COUNTING X-RAY DETECTOR

(71) Applicants: KONINKLIJKE PHILIPS N.V., Eindhoven (NL); PHILIPS DEUTSCHLAND GMBH, Hamburg (DE)

(72) Inventors: Ewald Roessl, Henstedt-Ulzburg (DE); Daerr Heiner, Hamburg (DE); Roger Steadman Booker, Aachen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 219 days.

(21) Appl. No.: 14/421,303

(22) PCT Filed: Jul. 15, 2013

(86) PCT No.: PCT/IB2013/055817
§ 371 (c)(1),
(2) Date: Feb. 12, 2015

(87) PCT Pub. No.: WO2014/027260
PCT Pub. Date: Feb. 20, 2014

(65) Prior Publication Data
US 2015/0234059 A1 Aug. 20, 2015

Related U.S. Application Data

(60) Provisional application No. 61/682,344, filed on Aug. 13, 2012.

(51) Int. Cl.
H05G 1/60 (2006.01)
G01T 1/24 (2006.01)
G01N 23/04 (2006.01)

(52) U.S. Cl.
CPC ........... G01T 1/247 (2013.01); G01N 23/046 (2013.01); G01T 1/248 (2013.01)

(58) Field of Classification Search
CPC ....... G01N 23/046; G01T 1/248; G01T 1/247; G01T 1/2928; H04N 5/32; A61B 6/4233
See application file for complete search history.

(56) References Cited

U.S. PATENT DOCUMENTS 5,382,824 A 1/1995 Popovic
7,268,354 B2 9/2007 Heismann et al.
(Continued)

FOREIGN PATENT DOCUMENTS

WO 2009/031126 3/2009
WO 2010043926 A1 4/2010
WO 2012041659 A1 4/2012

OTHER PUBLICATIONS

Roessl et al: "A Comparative Study of a Dual-Energy-Like Imaging Technique Based on Counting-Integrating Readout"; Med. Phys. 38 (12), Dec. 2011, pp. 6416-6428.

Primary Examiner — Courtney Thomas

(57) ABSTRACT

The invention relates to a method and an X-ray detector (100) for detecting incident X-ray photons (X). The X-ray detector (100) comprises at least one sensor unit (105) in which X-ray photons (X) are converted into sensor signals (s) and at least one flux sensor (104) for generating a flux signal (f) related to the flux of photons (X). The sensor signals (s) are corrected based on the flux signal (f). In a preferred embodiment, the sensor signals (s) represent a spectrally resolved pulse counting. The flux sensor (104) may be integrated into an ASIC (103) that is coupled to the sensor unit (105).

10 Claims, 2 Drawing Sheets

(56) References Cited

U.S. PATENT DOCUMENTS

| | | |
|---|---|---|
| 7,723,694 B2 | 5/2010 | Frach et al. |
| 2007/0206721 A1* | 9/2007 | Tkaczyk ................ A61B 6/032 378/19 |
| 2007/0262251 A1 | 11/2007 | Balan |
| 2010/0012845 A1 | 1/2010 | Baeumer et al. |
| 2011/0116595 A1 | 5/2011 | Carmi et al. |

* cited by examiner

PHOTON COUNTING X-RAY DETECTOR

CROSS-REFERENCE TO PRIOR APPLICATIONS

This application is the U.S. National Phase application under 35 U.S.C. §371 of International Application No., PCT/IB2013/055817, filed on Jul. 15, 2013, which claims the benefit of U.S. Provisional Patent Application No. 61/682,344, filed on Aug. 13, 2012. These applications are hereby incorporated by reference in their entirety herein.

FIELD OF THE INVENTION

The invention relates to an X-ray detector and a method for the detection of incident X-ray photons. Moreover, it relates to an imaging system comprising such an X-ray detector.

BACKGROUND OF THE INVENTION

The U.S. Pat. No. 7,268,354 B2 discloses an X-ray detector with a plurality of detector elements for counting incident X-ray photons. In order to improve the linearity of the detector elements, correction factors are determined in advance. A problem of this approach is that the behavior of the detector may drift over time such that the determined correction factors may become inappropriate.

SUMMARY OF THE INVENTION

It is an object of the invention to provide means that allow for a more accurate determination of X-radiation and an improved dynamic range.

This object is achieved by an X-ray detector according to claim 1, a method according to claim 2, and an imaging system according to claim 3. Preferred embodiments are disclosed in the dependent claims.

According to a first aspect, the invention relates to an X-ray detector for the detection of incident X-ray photons, said detector comprising the following components:

At least one sensor unit for the conversion of incident X-ray photons into electrical signals, said signals being called "sensor signals" in the following for purposes of reference.

At least one flux sensor for generating a signal, called "flux signal" in the following, that is related to the flux of incident X-ray photons.

A data processing system for evaluating the sensor signals based on the flux signal.

The described X-ray detector preferably comprises a plurality of sensor units that are arranged in a one- or two-dimensional array for detecting incident X-radiation in a spatially resolved way. When an image is generated with the sensor signals, for example a projection image of an object traversed by the X-radiation, the sensor units typically correspond to the pixels of such an image.

In general, different parts (beams) of the X-radiation incident on the X-ray detector may hit the sensor unit and the flux sensor, respectively. In a preferred embodiment, the sensor unit and the flux sensor are however hit by the same incident X-ray beam. Alternatively, the flux sensor may be exposed to the whole X-radiation, thus providing a flux signal related to the overall flux.

Moreover, one or more sensor units may be associated to one or more flux sensors, with the number of sensor units being lower, equal, or higher than the number of associated flux sensors. Accordingly, the flux signal of a given flux sensor may be used to evaluate (i) the sensor signal of just a single sensor unit, or (ii) the sensor signals of several sensor units. Similarly, the sensor signal of a given sensor unit may be evaluated by taking into account (i) the flux signal of just a single flux sensor, or (ii) the flux signals of several flux sensors.

In the context of the present application, the term "flux" shall denote the number of incident X-ray photons per unit area and time (measured e.g. in photons/$m^2$s). The "flux signal" may directly represent the flux of incident X-ray photons, or some other quantity related thereto (e.g. the intensity of the incident X-radiation in W/$m^2$).

The data processing system may be realized by dedicated electronic hardware, digital data processing hardware with associated software, or a mixture of both. The "evaluation" of the sensor signals based on the flux signal may especially comprise a correction of the sensor signals, for example the correction for non-linearities in the value of the sensor signal (output) in dependence on the flux of incident X-ray photons (input). In particular, it is possible to correct for a saturation of the sensor signal at high fluxes or for an ambiguity of the sensor signal. The evaluation may further comprise steps known in the art of X-ray data processing, for example the digitization of signals and/or the reconstruction of volume images from a plurality of projections obtained under different viewing angles.

According to a second aspect, the invention relates to a method for the detection of incident X-ray photons, said method comprising the following steps which may be executed in the listed or any other appropriate order:

a) The conversion of incident X-ray photons into electrical sensor signals.

b) The generation of a flux signal that is related to the flux of incident X-ray photons.

c) The evaluation of the sensor signals based on the flux signals.

Step a) of the method may preferably be done with the help of a sensor unit, step b) may preferably be done with at least one flux sensor, and step c) may preferably be done with a data processing system. The method may particularly be executed with an X-ray detector of the kind described above.

The invention further relates to an imaging system, for example a Computed Tomography (CT) system, particularly a spectrally resolved photon counting CT system. The imaging system comprises the following components:

An X-ray source.

An X-ray detector of the kind described above, i.e. with at least one sensor unit for converting incident X-ray photons into electrical sensor signals, at least one flux sensor for generating a flux signal related to the flux of incident X-radiation, and a data processing system for evaluating the sensor signals based on the flux signal. Optionally, the X-ray detector may be designed according to any of its preferred embodiments described below.

When X-rays are directed from the X-ray source through an object located in an imaging region towards the X-ray detector, projection images of said object can be generated with the imaging system.

The X-ray detector, the method, and the X-ray imaging system are based on the same inventive concept, i.e. the evaluation/correction of sensor signals of a sensor unit based on a flux signal measured (or obtained) in parallel. Accordingly, explanations provided for one of the X-ray detector, the method, or the imaging system are valid for the other elements, too.

The X-ray detector, the method, and the imaging system according to the invention have the advantage that flux related influences on the sensor signals provided by the sensor unit(s) can dynamically be corrected for because a flux signal is measured in parallel. This allows for example to improve the linearity of the detector output, or to resolve ambiguities that may occur in the raw sensor signals, e.g. due to a paralyzable detector behavior where the input count rate cannot be identified without ambiguity from the measured count rate.

In the following, various preferred embodiments of the invention will be described that relate to the X-ray detector, the method, and the imaging system described above.

In general, the sensor unit and the flux sensor may be disposed relative to each other in any arrangement. In a preferred embodiment, they will however be aligned with respect to the main direction of X-ray incidence, wherein said "main direction" may be defined as the average of all directions of incident X-rays. Typically, these directions will be highly correlated because the incident radiation has only a limited divergence. In many cases, the main direction of X-ray incidence may simply be identified with the direction connecting the (centre of gravity of the) X-ray source with the (centre of gravity of the) sensor unit.

The aforementioned alignment of the sensor unit and the flux sensor with respect to the main direction of X-ray incidence implies that (most or all of) the X-ray photons which impinge onto the sensor unit will also hit the flux sensor (if they are not beforehand absorbed in the sensor unit) or vice versa (in the less preferred case that the flux sensor is arranged in front of the sensor unit). The flux sensor will hence be exposed to the same part of the incident X-radiation as the sensor unit, which allows to correct the sensor signals individually in a spatially resolved way.

In a preferred embodiment of the invention, the sensor unit comprises a conversion material for converting incident X-ray photons into charge signals, e.g. into electron-hole pairs in the conduction resp. valence band of the conversion material.

The aforementioned conversion material may preferably comprise a semiconducting material selected from the group consisting of pure group IV-elements (like silicon (Si), Selenium (Se), or Germanium (Ge), semiconducting compounds from the types I-VII (like sodium iodide (NaI)), II-VI (like Cadmium Telluride (CdTe) or Cadmium-Zinc-Telluride ($Cd_xZn_{1-x}Te$ or CZT)), III-V (like Gallium Arsenide (GaAs), or IV-VI (like Lead Oxide (PbO)). Most preferred, the conversion material consists of a semiconductor with high X-ray or γ-ray absorption capabilities and high charge mobilities as for example CdTe and CZT.

At least one electrode may be coupled to the conversion material for sensing the generated charge signals. Moreover, electrodes on opposite sides of the conversion material may be operated as anode(s) and cathode(s) to generate an electrical field in the conversion material along which generated charge signals can travel until they reach one of the electrodes.

In another embodiment of the invention, the data processing system may comprise a processing circuit located adjacent to the sensor unit(s) for collecting and processing the sensor signals of the sensor unit(s). If the sensor unit is a direct-conversion unit designed according to the above mentioned embodiment, i.e. comprising a conversion material with electrodes, the processing circuit may particularly be bonded to these electrodes. The processing circuit may then provide a first, elementary processing of the sensor signals, for example a signal digitization or a pulse counting.

The processing circuit may particularly be an integrated circuit, for instance an Application Specific Integrated Circuit (ASIC). Attachment to the electrodes on a conversion material may then for example be achieved by flip-chip bonding.

The flux sensor may in general have any design that provides a sufficient sensitivity in the spectral range of the X-ray photons to be measured. Preferably, the flux sensor may comprise an element selected from the group consisting of a PIN diode, a GaAs diode, and a Si-PM array.

According to another embodiment, the flux sensor may comprise a scintillating material for converting incident X-ray photons into photons of lower wavelength, e.g. into visible light. The photons of lower wavelength can then for example be detected by a (light-sensitive) photodiode. In a preferred embodiment, a (thin) layer of scintillating material may be associated to a plurality of separate photodiodes.

The data processing system (particularly the above mentioned processing circuit, if present) may preferably be adapted to count pulses of sensor signals generated by (single) X-ray photons. Thus a pulse counting (or "photon counting") X-ray detector is provided which achieves a high accuracy. Due to hardware limitations, such a pulse counting detector is however prone to problems like non-linearities and saturation at high pulse rates. It is therefore particularly favorable that an X-ray detector according to the present invention allows for a flux related correction of sensor signals.

According to a further development of the aforementioned embodiment, the pulses of sensor signals are counted in a spectrally resolved way (i.e. resolved with respect to the energy spectrum of the incident X-ray photons). Pulse parameters like the pulse height may for example indicate the energy deposited by the detected X-ray photons, such that pulse-height discrimination enables the intended spectral resolution.

It was already mentioned that the evaluation of the sensor signals based on the flux signal can particularly be or comprise a correction of the sensor signal. In a preferred embodiment, calibration data of the sensor signals and the corresponding flux signals are used to correct a measurement in such a way that the sensor output curve is linearized. The calibration data can for example be obtained by measuring sensor and flux signals simultaneously for the same (known) incident X-radiation r. Moreover, "linearization of the sensor output curve" means that the corrected sensor signal s' depend (approximately) linearly on the incident X-radiation r.

BRIEF DESCRIPTION OF THE DRAWINGS

These and other aspects of the invention will be apparent from and elucidated with reference to the embodiments described hereinafter.

In the drawings.

Like reference numbers or numbers differing by integer multiples of 100 refer in the Figures to identical or similar components.

DETAILED DESCRIPTION OF EMBODIMENTS

Photon counting spectral CT faces the challenges of having to cope with very high X-ray flux rates, conditions under which even the best counting detectors build from CdTe or CZT behave in an intrinsically non-linear way due to pulse-pileup and dead-time effects. Depending on the detector electronics the behavior of the detectors can be modeled by the paralyzable or non-paralyzable detector behavior. In both cases the deviations from linearity are small as long as the rates remain smaller than the inverse deadtime but behave very differently around or above that level.

For example, the output count rate m of a paralyzable detector is a function of the input count rate r (number of incident X-ray photons per time) and a parameter $\tau$ which is related to the width of the pulses generated by the detector. It is theoretically given by the formula $$m = r \exp(-r\tau).$$

Figure 1:
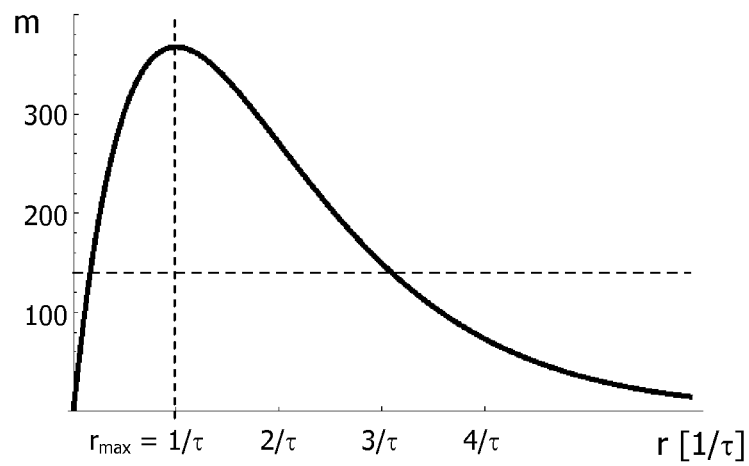
FIG. 1 shows the measured output count rate m as a function of the input count rate r for a counting X-ray detector.

FIG. 1 shows the curve corresponding to this formula, which has a maximum at $r_{max} = 1/\tau$. For one measurement of the output count rate m there exist two corresponding input count rates r, one below $r_{max}$ and one above $r_{max}$. For reconstructing an image, it is absolutely necessary to know whether the input rate r is below or above $r_{max}$ as the corrected rates typically differ significantly. It would therefore be very beneficial if a measure of the overall flux were available to correct for the rate induced non-linearities in the counting results.

As a possible solution to the above problem the present invention proposes to integrate a flux sensor, for example a conventional photodiode, into the detector. In particular, a photodiode may be integrated into the counting ASIC which is typically flip-chip bonded to the X-ray sensor units. Despite the attenuation by the sensor, the photodiode will still receive an X-ray flux sufficiently large to provide a signal for correcting for the non-linearities in the counting AISC output, in particular as the corrections will be large only in the high flux regime with reasonable signal on the X-ray flux sensor. In a paralyzable detector this simple arrangement could for example be used to resolve the ambiguity of the determination of the input rate r from a given output rate m measurement.

Figure 2:
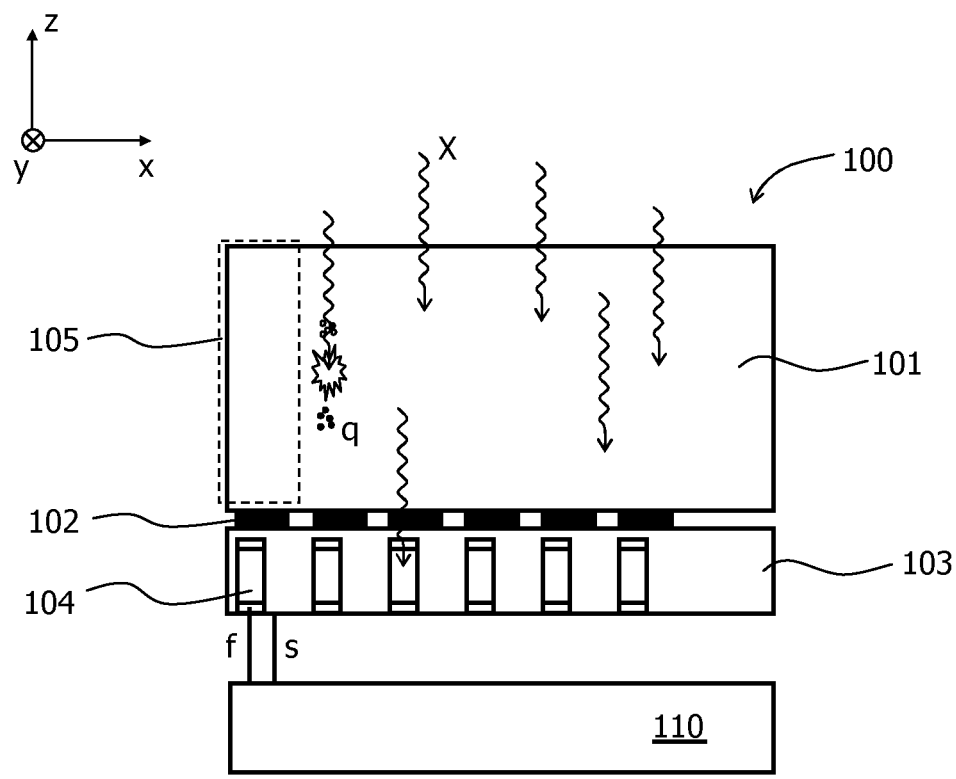
FIG. 2 schematically shows a section through an X-ray detector according to the present invention in which photodiodes are integrated into an ASIC.

FIG. 2 shows an exemplary embodiment of an X-ray detector 100 that is designed according to the above principles. The X-ray detector 100 comprises a direct conversion material 101, for example a block (crystal) of CdTe or CZT. The top face of this block is exposed to X-ray photons X incident from above along the (negative) z-direction. The X-rays may for example come from an X-ray source (not shown) and may have traversed an object (not shown) to be imaged. Within the conversion material 101, the X-ray photons X may be converted into charge signals q, for example electron-hole pairs in the conduction resp. valence band of the conversion material.

The aforementioned charge signals q move along the direction of an electrical field that is generated by electrodes on opposite sides of the conversion material 101. For example, a plurality of electrodes 102 may be disposed at the bottom side of the conversion material 101, and a (single) counter-electrode on its top side (not shown). An electrical field in z-direction can then be generated between these electrodes, and charge signals q generated within the conversion material 101 will be transported to the corresponding electrodes 102, where they generate an electrical signal s indicative of the X-ray conversion.

A plurality of sensor units 105 (only one of which is indicated in FIG. 2 by dashed lines) is thus effectively defined within the conversion material 101, wherein each sensor unit 105 is associated to a corresponding bottom electrode 102 where charge signals q generated in the volume of the sensor unit are collected and transformed into sensor signals s (e.g. a current pulse).

An ASIC 103 is flip-chip bonded to the above mentioned electrodes 102 on the bottom side of the conversion material 101. The ASIC comprises the hardware necessary for a primary processing (e.g. pulse counting and/or discrimination) of the sensor signals s generated at the electrodes 102.

Furthermore, a plurality of photodiodes 104 (e.g. Si-PIN diodes) is provided in the bulk material of the ASIC 103, wherein just one photodiode 104 is associated to each sensor unit 105. Seen in the main direction of X-ray incidence (negative z-direction), the photodiodes 104 are aligned with the sensor units 105. Accordingly, each sensor unit 105 is associated to just one photodiode 104. The photodiodes 104 generate a "flux signal" f that is related to the flux of X-ray photons impinging onto the corresponding photodiode 104 (after passage through the conversion material). The flux signal f can then be exploited for the evaluation, particularly the correction of the sensor signals s. This evaluation may take place in the ASIC 103 and/or in a separate (digital) data processing device 110 that is coupled to the ASIC 103.

The aforementioned correction of sensor signals s may for example comprise a resolution of the ambiguity illustrated in FIG. 1. In this case the sensor signal s corresponds to a measured output count rate m, s=m, wherein it is not clear if the associated input count rate r is above or below $r_{max}$. The (coarse) measurement of the flux by the photodiodes 104 (i.e. the flux signal f) provides just this information, i.e. if $r < r_{max}$ or $r > r_{max}$. Once this is known, the input count rate r can be determined unambiguously and with high accuracy from the sensor signal s.

For the case where the photodiodes are integrated into the ASIC, a typical front-side CMOS process could be used, however with the restriction of very thin epitaxial layers. In case the bulk of the wafer is used the design would resemble a typical back-illuminated photodiode. Each channel of the ASIC would need to be equipped with an individual photodiode. Due to the relatively low atomic number of silicon, the exact location of the diode along the z-direction inside the ASIC is not important. Due to attenuation of the conversion material itself however the active diode volume should be maximized. Instead of a typical PIN photodiode, Si-PM arrays could be used, too.

Figure 3:
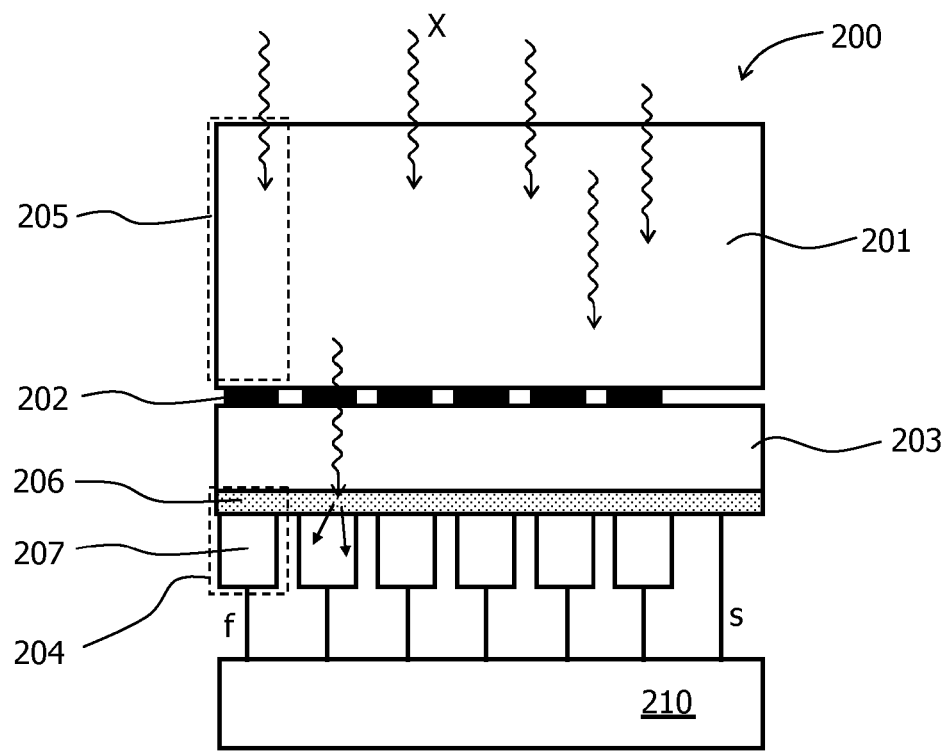
FIG. 3 schematically shows a section through another X-ray detector according to the present invention in which a scintillator material and photodiodes are disposed below an ASIC.

Instead of being directly integrated into the ASIC 103, as show in FIG. 2, the photodiodes could also be placed below the actual ASIC. This is illustrated in FIG. 3 for an alternative X-ray detector 200 according to the present invention. The design of this detector 200 is identical or similar to that of the detector 100 (FIG. 2) and will therefore not be described in detail again. A difference to the previous embodiment is that the flux sensors 204 which provide the flux signals f are now disposed below the ASIC 203.

For the case where photodiodes are placed below the ASIC, a photodiode free of choice in thickness and material can be used. The ASIC typically absorbs less than 2% of the radiation leaving the sensor. For example, after attenuation of the X-ray primary beam by a 1.6 mm of CdTe as conversion material 101 followed by the ASIC 103, an incident X-ray photon rate of about several Mcps is left at an area of about 0.5 mm×0.5 mm. A photodiode based on 3 mm GaAs has an efficiency of about 80% for absorbing this spectrum.

The flux sensors 204 shown in FIG. 3 could be diodes that directly convert X-rays with the aforementioned characteristics. However, FIG. 3 actually illustrates another embodiment, in which a thin slab 206 of scintillating material is disposed between the ASIC 203 and a plurality of photodiodes 207. This scintillator layer 206 converts incident X-rays into photons of lower wavelength, e.g. of visible light, which can more readily be detected by (light-sensitive) photodiodes 207. A flux sensor 204 is then constituted by a photodiode 207 and a corresponding volume of the scintillator layer 206 (the volume from which the photodiode receives light).

The additional layer of scintillating material could optionally be arranged at other positions, too. In particular, an additional layer of scintillating material can be brought onto the ASIC waver from top and/or from the bottom, or it may be deposited on the photodiode(s). Moreover, these arrangements can be combined with integrated photodiodes (104 in FIG. 2) or with external photodiodes (207 in FIG. 3). The stopping by the waver is in all cases irrelevant, and it is better to use a high Z scintillating material.

Figure 4:
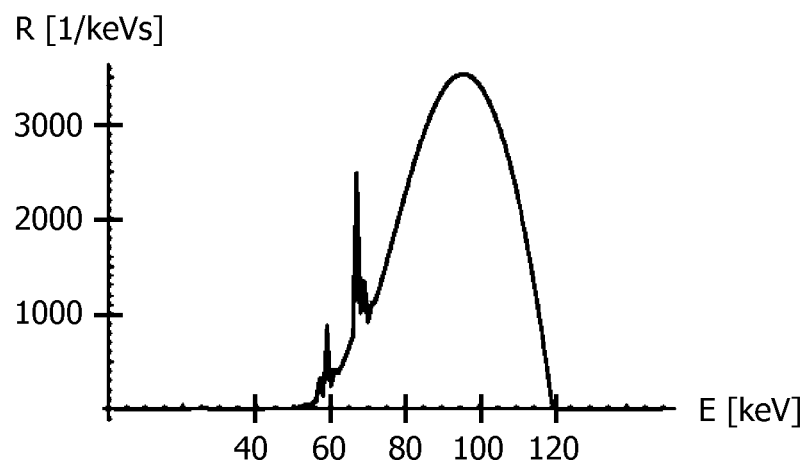
FIG. 4 shows a typical spectrum of X-ray photons incident on the flux sensors of the X-ray detector of FIG. 2 or 3.

FIG. 4 shows the effective X-ray spectrum "seen" by 0.5 mm silicon after attenuation of the X-ray primary beam by a 1.6 mm of CdTe as the sensor. The values are valid for a distance of 1040 mm from the focal spot of a CT X-ray tube with 400 mA tube current and 120 kVp voltage setting. The total estimated X-ray photon rate would be 130 kcps at a surface of 0.5 mm×0.5 mm. It should be noted that for X-rays attenuated by an object (e.g. a patient) this signal will drop very quickly. However, in those regions, the detector signal itself will not suffer from non-linearities due to the attenuation itself.

The approach of the present invention can particularly be applied to spectral detector systems with dedicated readout ASICs to be operated at X-ray high flux (in the order of several hundreds of Mcps and square millimeter).

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. An X-ray detector comprising:
at least one sensor unit for the conversion of incident X-ray photons (X) into electrical sensor signals (s),
wherein the sensor unit comprises a conversion material for converting incident X-ray photons (X) into charge signals (q),
and wherein at least one electrode is coupled to the conversion material for sensing the charge signals (q);
at least one flux sensor for generating a flux signal (f) that is related to the flux of incident X-ray photons (X);
a data processing system for evaluating the sensor signals (s) based on the flux signal (f), wherein
the data processing system comprises a processing circuit, that is located adjacent to the sensor unit and bonded to said electrode, for collecting and processing its sensor signals (s);
wherein the flux sensor is integrated into or placed below the processing circuit.

2. An X-ray imaging system, particularly a spectrally resolved photon counting CT system, comprising:
an X-ray source; and
an X-ray detector according to claim 1.

3. The X ray detector according to claim 1,
wherein the sensor unit and the flux sensor are aligned with respect to the main direction (z) of the X-ray incidence.

4. The X ray detector according to claim 1,
wherein the conversion material comprises a material selected from the group consisting of CdTe, CZT, Si, Ge, Se, GaAs, and PbO.

5. The X ray detector according to claim 1,
wherein the processing circuit comprises an integrated circuit.

6. The X ray detector according to claim 1,
wherein the flux sensor comprises an element selected from the group consisting of a PIN diode, a GaAs diode, and an Si-PM array.

7. The X ray detector according to claim 1,
wherein the flux sensor comprises a scintillating material.

8. The X ray detector according to claim 1,
wherein the data processing system is adapted to count pulses of sensor signals (s) generated by single X-ray photons (X).

9. The X ray detector according to claim 8,
wherein the pulses are counted in a spectrally resolved way.

10. The X ray detector according to claim 1,
wherein calibration data of the sensor signals (s) and the corresponding flux signals (f) are used to linearize the sensor output.

* * * * *